United States Patent
Martin et al.

(10) Patent No.: US 11,160,898 B2
(45) Date of Patent: Nov. 2, 2021

(54) VACUUM MEMBRANE THERMOFORMED POLY-4-HYDROXYBUTYRATE MEDICAL IMPLANTS

(71) Applicant: Tepha, Inc., Lexington, MA (US)

(72) Inventors: David P. Martin, Arlington, MA (US); Said Rizk, Windham, NH (US)

(73) Assignee: Tepha, Inc., Lexington, MA (US)

( * ) Notice: Subject to any disclaimer, the term of this patent is extended or adjusted under 35 U.S.C. 154(b) by 94 days.

(21) Appl. No.: 16/209,299

(22) Filed: Dec. 4, 2018

(65) Prior Publication Data
US 2019/0167834 A1    Jun. 6, 2019

Related U.S. Application Data

(60) Provisional application No. 62/594,191, filed on Dec. 4, 2017.

(51) Int. Cl.
*B29C 51/04* (2006.01)
*A61L 15/26* (2006.01)
(Continued)

(52) U.S. Cl.
CPC .............. *A61L 15/26* (2013.01); *A61L 27/18* (2013.01); *A61L 27/48* (2013.01); *A61L 27/54* (2013.01);
(Continued)

(58) Field of Classification Search
CPC .............. A61L 15/26; A61L 27/28; A61L 27/40–27/48; A61L 27/54–27/58;
(Continued)

(56) References Cited

U.S. PATENT DOCUMENTS

| 5,811,272 A | 9/1998 | Snell |
| 6,316,262 B1 | 11/2001 | Huisman |

(Continued)

FOREIGN PATENT DOCUMENTS

| WO | 2006076026 | 7/2006 |
| WO | 2011119742 | 9/2011 |

(Continued)

OTHER PUBLICATIONS

Hori, et al., "Chemical synthesis of high molecular weight poly(3-hydroxybutyrate-co-4-hydroxybutyrate)", Polymer 36:4703-5 (1995).

(Continued)

*Primary Examiner* — Paul B Prebilic
(74) *Attorney, Agent, or Firm* — Wolf, Greenfield & Sacks, P.C.

(57) ABSTRACT

Methods to produce thermoformed implants comprising poly-4-hydroxybutyrate homopolymer, copolymer, or blend thereof, including surgical meshes, have been developed. These thermoforms are preferably produced from porous substrates of poly-4-hydroxybutyrate homopolymer or copolymer thereof, such as surgical meshes, by vacuum membrane thermoforming. The porous thermoformed implant is formed by placing a porous substrate of poly-4-hydroxybutyrate homopolymer or copolymer thereof over a mold, covering the substrate and mold with a membrane, applying a vacuum to the membrane so that the membrane and substrate are drawn down on the mold and tension is applied to the substrate, and heating the substrate while it is under tension to form the thermoform. The method is particularly useful in forming medical implants of poly-4-hydroxybutyrate and copolymers thereof, including hernia meshes, mastopexy devices, breast reconstruction devices, and implants for plastic surgery, without exposing the (Continued)

resorbable implants to water and without shrinking the porous substrate during molding.

12 Claims, 1 Drawing Sheet

(51) Int. Cl.
| | |
|---|---|
| A61L 27/18 | (2006.01) |
| A61L 27/54 | (2006.01) |
| A61L 31/16 | (2006.01) |
| A61L 27/48 | (2006.01) |
| B29C 51/00 | (2006.01) |
| A61L 29/12 | (2006.01) |
| A61L 31/06 | (2006.01) |
| A61L 31/12 | (2006.01) |
| B29C 51/42 | (2006.01) |
| A61L 29/06 | (2006.01) |
| B29C 51/10 | (2006.01) |
| B29L 31/00 | (2006.01) |

(52) U.S. Cl.
CPC .............. *A61L 29/06* (2013.01); *A61L 29/126* (2013.01); *A61L 31/06* (2013.01); *A61L 31/126* (2013.01); *A61L 31/129* (2013.01); *A61L 31/16* (2013.01); *B29C 51/002* (2013.01); *B29C 51/421* (2013.01); *B29C 51/10* (2013.01); *B29C 2791/006* (2013.01); *B29L 2031/753* (2013.01); *B29L 2031/7532* (2013.01)

(58) Field of Classification Search
CPC ........ A61L 29/06; A61L 29/12–29/126; A61L 31/06; A61L 31/129; A61L 2300/404; A61L 2300/406; A61L 2300/408; A61L 2300/44; A61L 2300/80; A61L 2300/802; A61L 27/18; B29C 51/002; B29C 51/004; B29C 51/10; B29C 51/105; B29C 51/145; B29C 51/18; B29C 51/42; B29C 51/426; B29C 55/005; B29C 55/023; B29C 2791/006
See application file for complete search history.

(56) References Cited

U.S. PATENT DOCUMENTS

| | | | |
|---|---|---|---|
| 6,323,010 B1 | 11/2001 | Skraly | |
| 6,514,515 B1 | 2/2003 | Williams | |
| 6,548,569 B1 | 4/2003 | Williams | |
| 6,555,123 B2 | 4/2003 | Williams | |
| 6,585,994 B2 | 7/2003 | Williams | |
| 6,610,764 B1 | 8/2003 | Martin | |
| 6,623,748 B2 | 9/2003 | Clokie | |
| 6,746,685 B2 | 6/2004 | Williams | |
| 6,828,357 B1 | 12/2004 | Martin | |
| 6,838,493 B2 | 1/2005 | Williams | |
| 6,867,247 B2 | 3/2005 | Williams | |
| 6,867,248 B1 | 3/2005 | Martin | |
| 6,878,758 B2 | 4/2005 | Signer | |
| 7,025,980 B1 | 4/2006 | Williams | |
| 7,179,883 B2 | 2/2007 | Williams | |
| 7,244,442 B2 | 7/2007 | Williams | |
| 7,268,205 B2 | 9/2007 | Williams | |
| 7,553,923 B2 | 6/2009 | Williams | |
| 7,618,448 B2 | 11/2009 | Schmitz | |
| 7,641,825 B2 | 1/2010 | Rizk | |
| 7,906,135 B2 | 3/2011 | Williams | |
| 7,943,683 B2 | 5/2011 | Rizk | |
| 8,016,883 B2 | 9/2011 | Coleman | |
| 8,034,270 B2 | 10/2011 | Martin | |
| 8,039,237 B2 | 10/2011 | Martin | |
| 8,084,125 B2 | 12/2011 | Rizk | |
| 8,231,889 B2 | 7/2012 | Williams | |
| 8,287,909 B2 | 10/2012 | Martin | |
| 8,680,228 B2 | 3/2014 | Guo | |
| 8,747,468 B2 | 6/2014 | Martin | |
| 8,753,555 B2 | 6/2014 | Rizk | |
| 8,758,657 B2 | 6/2014 | Martin | |
| 8,771,720 B2 | 7/2014 | Williams | |
| 9,125,719 B2 | 9/2015 | Martin | |
| 9,149,561 B2 | 10/2015 | Rizk | |
| 9,290,612 B2 | 3/2016 | Martin | |
| 9,302,029 B2 | 4/2016 | Ganatra | |
| 9,326,841 B2 | 5/2016 | Martin | |
| 9,333,066 B2 | 5/2016 | Martin | |
| 9,457,127 B2 | 10/2016 | Martin | |
| 9,480,780 B2 | 11/2016 | Martin | |
| 9,532,867 B2 | 1/2017 | Felix | |
| 9,555,155 B2 | 1/2017 | Ganatra | |
| 9,687,585 B2 * | 6/2017 | Bernasconi | .......... A61L 31/129 |
| 2007/0182041 A1 | 8/2007 | Rizk | |
| 2012/0271396 A1 | 10/2012 | Zheng | |
| 2014/0100649 A1 | 4/2014 | Gada | |
| 2015/0056131 A1 | 2/2015 | Bernasconi | |
| 2015/0057368 A1 | 2/2015 | Connelly | |
| 2015/0313700 A1 | 11/2015 | Rizk | |

FOREIGN PATENT DOCUMENTS

| | | |
|---|---|---|
| WO | 2013049161 | 4/2013 |
| WO | 2015006737 | 1/2015 |

OTHER PUBLICATIONS

Houk, et al., "Why delta-valerolactone polymerizes and gamma-butyrolactone does not polymerize", J. Org. Chem., 2008, 73 (7):2674-8 (2005).
Martin, et al., "Medical Applications of Poly-4hydroxybutyrate: A Strong Flexible Absorbable Biomaterial", Biochem. Eng. J., 16:97-105 (2003).
Martin, et al., "Characterization of poly-4-hydroxybutyrate mesh for hernia repair applications," J. Surg. Res., 184:766-73 (2013).
Moore, et al., "Chemosynthesis of bioresorbable poly(gamma-butyrolactone) by ring-opening polymerisation: a review", Biomaterials 26:3771-3782 (2005).
Odermatt, et al.,"A new long-term absorbable monofilament suture made from poly-4-hydroxybutyrate", Int J Polym Sci., 12:Article ID 216137 (2012).
Steinbuchel, "Diversity of bacterial polyhydroxyalkanoic acids", FEMS Microbial. Lett. 128:219-28 (1995).
Williams, et al., "Poly-4-hydroxybutyrate (P4HB): a new generation of resorbable medical devices for tissue repair and regeneration", Biomed. Tech. (Berl) 58(5):439-452 (2013).
Williams, et al., "Controlled hydrolysis of poly-4-hydroxybutyrate and copolymers", Polyesters, III, 4:91-127 (2002).
International Search Report PCT/US2018/063551 dated Mar. 7, 2019.

* cited by examiner

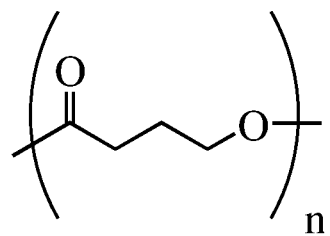

VACUUM MEMBRANE THERMOFORMED POLY-4-HYDROXYBUTYRATE MEDICAL IMPLANTS

CROSS-REFERENCE TO RELATED APPLICATIONS

This application claims the benefit of and priority to U.S. Ser. No. 62/594,191, filed on Dec. 4, 2017, which is hereby incorporated herein by reference in its entirety.

FIELD OF THE INVENTION

The present invention generally relates to vacuum membrane thermoforming of poly-4-hydroxybutyrate and copolymers thereof, the compositions used to produce these thermoforms, and the processes used to produce these thermoforms, as well as their use in many types of implant applications including wound management, general surgery including hernia repairs and anti-adhesion devices, tissue engineering, plastic and reconstructive surgery, drug delivery, pelvic floor reconstruction, orthopedic surgery, and vascular and cardiovascular surgery.

BACKGROUND OF THE INVENTION

Vacuum thermoforming is a manufacturing process where a plastic sheet is heated to a pliable forming temperature, placed or stretched onto a mold, and shaped against the mold by applying a vacuum. The molded shape may be trimmed if necessary to create a usable product. The sheet, or "film" when referring to thinner gauges and certain material types, is generally heated in an oven to a high-enough temperature that it can be stretched into or onto a mold and cooled to a finished shape. In its simplest form, a small tabletop or lab size machine can be used to heat small cut sections of plastic sheet and stretch it over a mold using vacuum. This method is often used for sample and prototype parts. In complex and high-volume applications, very large production machines are utilized to heat and form the plastic sheet and trim the formed parts from the sheet in a continuous high-speed process, and can produce many thousands of finished parts per hour depending on the machine and mold size and the size of the parts being formed.

Vacuum membrane thermoforming differs from vacuum thermoforming and other forms of processing plastics, such as injection molding, blow molding, and rotational molding. In vacuum membrane thermoforming, a plastic substrate, such as a film, is placed on a mold, the plastic substrate is covered with a membrane, and shaped against the mold as the membrane is drawn down on the top of the plastic substrate by the vacuum. In this variation of thermoforming, the membrane forms an air-tight seal over the plastic substrate, and applies a force across the surface area of the plastic substrate to mold the substrate into the desired shape. As with vacuum thermoforming, the plastic substrate is typically heated to a molding temperature prior to applying the vacuum.

Not every polymer is suitable for vacuum membrane thermoforming. Each polymer has different properties. Amorphous polymers are preferred, melt temperatures are critical, and physical properties significantly impact the resulting products.

There is a need for methods to rapidly and inexpensively mold biodegradable polymeric substrates, including biodegradable polymeric meshes, for use in medical implants. For example, there is a need to prepare three-dimensional polymeric mesh implants. US 20150313700 to Rizk et al. discloses split metal molds that can be used to prepare three-dimensional mesh implants made from poly-4-hydroxybutyrate (Tepha's P4HB™ polymer). The method however involves heating the mesh by immersing a mold containing the mesh in a hot water bath, and subsequently drying the mesh.

US Patent Application No. 20150056131 to Bernasconi, et al. discloses methods to thermoform poly-4-hydroxybutyrate films, sheets, and laminates made from a poly-4-hydroxybutyrate film and a poly-4-hydroxybutyrate mesh. The method disclosed preferably involves pre-heating pre-cut films or sheets of poly-4-hydroxybutyrate, and then molding the heated films or sheets. The method does not disclose how to thermoform a porous plastic substrate, such as a mesh, or how to use vacuum membrane thermoforming to mold a porous poly-4-hydroxybutyrate mesh. The method also does not disclose how to thermoform a porous mesh without the mesh shrinking.

Thus, there is currently no disclosure of how a porous substrate of poly-4-hydroxybutyrate or copolymer thereof, such as a mesh, can be thermoformed, the equipment necessary to thermoform the porous substrate, the conditions necessary to thermoform a poly-4-hydroxybutyrate homopolymer or copolymer mesh or the properties of a thermoformed poly-4-hydroxybutyrate homopolymer or copolymer mesh. There is also no disclosure of thermoforms produced from poly-4-hydroxybutyrate homopolymer or copolymer meshes with desirable properties for use as implants.

It is therefore an object of the present invention to provide a means of thermoforming a porous substrate of poly-4-hydroxybutyrate or copolymer thereof, such as a mesh without compromising the porosity of the mesh.

It is another object of the present invention to provide porous thermoforms of poly-4-hydroxybutyrate homopolymer or copolymer thereof produced by vacuum membrane thermoforming characterized by specific physical properties.

It is a further object of the present invention to provide porous medical implants of poly-4-hydroxybutyrate and copolymer thereof with enhanced mechanical properties and controlled degradation profiles that can be used in medical applications.

SUMMARY OF THE INVENTION

Methods to produce porous thermoformed implants comprising poly-4-hydroxybutyrate homopolymer or copolymer thereof, including surgical meshes, have been developed. These thermoforms are preferably produced from porous substrates of poly-4-hydroxybutyrate homopolymer or copolymer thereof, such as surgical meshes, by vacuum membrane thermoforming under conditions that do not compromise the porosity of the porous substrate. In a preferred embodiment, the porous thermoformed implant is formed by placing a porous substrate of poly-4-hydroxybutyrate homopolymer or copolymer thereof over a mold, covering the substrate and mold with a membrane, applying a vacuum to the membrane so that the membrane and substrate are drawn down on the mold and tension is applied to the substrate to shape the substrate, and heating the shaped substrate while it is under tension to form the thermoform. The method is particularly useful in forming medical implants of poly-4-hydroxybutyrate and copolymers thereof, including hernia meshes, mastopexy devices, breast reconstruction devices, and implants for plastic surgery, without exposing the resorbable implants to water and without shrinking the porous substrate during molding. In a particularly preferred embodiment the thermoforms are produced by a process that includes heating the porous substrates under tension at a temperature equal to or greater than the softening point of poly-4-hydroxybutyrate, but less than 150° C.

BRIEF DESCRIPTION OF THE DRAWINGS

FIG. 1 shows the chemical structure of poly-4-hydroxybutyrate.

DETAILED DESCRIPTION OF THE INVENTION

Definitions

"Bioactive agent" is a substance used, for example, for the treatment, prevention, diagnosis, cure, or mitigation of disease or disorder, a substance that affects the structure or function of the body, or pro-drugs, which become biologically active or more active after they have been placed in a predetermined physiological environment. Bioactive agents include biologically, physiologically, or pharmacologically active substances that act locally or systemically in the human or animal body. Examples can include, but are not limited to, small-molecule drugs, anti-inflammatory agents, immunomodulatory agents, molecules that affect cell migration, molecules that affect cell division, molecules that affect cell proliferation and differentiation, molecules that stimulate phenotypic modification of cells, molecules that affect angiogenesis, molecules that affect vascularization, molecules that affect extracellular matrix disposition, signaling ligands, platelet rich plasma polymers, peptides, proteins, antibodies, growth factors, fibronectin, laminin, vitronectin, integrins, antimicrobials, antibiotics, steroids, hydroxyapatite, silver particles, vitamins, non-steroidal anti-inflammatory drugs, chitosan and derivatives thereof, alginate and derivatives thereof, collagen, sugars, polysaccharides, nucleotides, oligonucleotides, lipids, hyaluronic acid and derivatives thereof, antisense molecules, aptamers, siRNA, nucleic acids, and combinations thereof. "Bioactive agent" includes a single such agent and is also intended to include a plurality.

"Biocompatible" as generally used herein means the biological response to the material or device being appropriate for the device's intended application in vivo. Any metabolites of these materials should also be biocompatible.

"Blend" as generally used herein means a physical combination of different polymers, as opposed to a copolymer formed of two or more different monomers.

"Burst strength" as used herein is determined, unless otherwise specified, according to ASTM D6797-02 (Standard Test Method for Bursting Strength of Fabrics Constant-Rate-of-Extension (CRE) Ball Burst Test) at ambient conditions using a ball burst fixture with a 1.6 cm circular opening and a 1 cm diameter half-rounded probe.

"Copolymers of poly-4-hydroxybutyrate" as generally used herein means any polymer including 4-hydroxybutyrate with one or more different hydroxy acid units.

"Elongation to break" as used herein means the increase in length of a material that occurs when tension is applied to break the material. It is expressed as a percentage of the material's original length.

"Endotoxin units" as used herein are determined using the limbus amebocyte lysate (LAL) assay as further described by Gorbet et al. Biomaterials, 26:6811-6817 (2005).

Fiber dimeter as generally defined herein is determined according to the US Pharmacopeia (USP) standard for diameter of surgical sutures (USP 861).

"Implant" as generally used herein include medical devices that are used in vivo as well as those that contact the surface of the body or are inserted into any orifice of the body.

"Molecular weight" as used herein, unless otherwise specified, refers to the weight average molecular weight (Mw), not the number average molecular weight (Mn), and is measured by GPC relative to polystyrene.

"Poly-4-hydroxybutyrate" as generally used herein means a homopolymer of 4-hydroxybutyrate units. It may be referred to herein as Tepha's P4HB™ biomaterial or Tepha-FLEX® biomaterial (manufactured by Tepha, Inc., Lexington, Mass.). Poly-4-hydroxybutyrate includes the monomer units with naturally occurring ratios of carbon, hydrogen and oxygen isotopes, as well as monomer units with specific quantities of these isotopes, i.e. that have been isotopically enriched. For example, the homopolymers may include one or more monomers that have been fully or partially deuterated at any position in the monomer.

"Resorbable" as generally used herein means the material is broken down in the body and eventually eliminated from the body. The terms "resorbable", "degradable", "erodible", and "absorbable" are used somewhat interchangeably in the literature in the field, with or without the prefix "bio". Herein, these terms will be used interchangeably to describe material broken down and gradually absorbed or eliminated by the body, whether degradation is due mainly to hydrolysis or mediated by metabolic processes.

"Softening Point" as used herein means the Vicat softening point determined according to test method ASTM D1525-09. The softening point is measured as the temperature at which a polymer is penetrated to a depth of 1 mm by a flat-ended needle with a 1 sq mm circular or square cross-section under a load of 9.81 N.

"Suture pullout strength" as used herein means the peak load (kg) at which an implant fails to retain a suture. It is determined using a tensile testing machine by securing an implant in a horizontal holding plate, threading a suture in a loop through the implant at a distance of 1 cm from the edge of the implant, and securing the suture arms in a fiber grip positioned above the implant. Testing is performed at a crosshead rate of 100 mm/min, and the peak load (kg) is recorded. The suture is selected so that the implant will fail before the suture fails. The suture pullout strength may be converted and expressed as Newtons.

"Taber Stiffness Unit" is defined as the bending moment of ⅕ of a gram applied to a 1½" (3.81 cm) wide specimen at a 5 cm test length, flexing it to an angle of 15°, and is measured using a Taber V-5 Stiffness Tester Model 150-B or 150-E. The TABER® V-5 Stiffness Tester—Model 150-B or 150-E is used to evaluate stiffness and resiliency properties of materials up to 10,000 Taber Stiffness Units. This precision instrument provides accurate test measurement to ±1.0% for specimens 0.004" to 0.219" thickness. One Taber Stiffness Unit is equal to 1 gram cm (g cm) or 0.0981 milliNewton meters (mN m). Taber Stiffness Units can be converted to Genuine Gurley™ Stiffness Units with the equation: $S_T=0.01419S_G-0.935$, where $S_T$ is the stiffness in Taber Stiffness Units and $S_G$ is the stiffness in Gurley Stiffness Units. To convert Taber Stiffness Units to Millinewton Meters, use the equation: $X=S_T \cdot 0.098067$, where X is the stiffness in Millinewton Meters.

"Vacuum membrane thermoforming" as used herein refers to a method for preparing a shaped article from a thermoplastic substrate, preferably a porous substrate. In vacuum membrane thermoforming, a plastic substrate is placed on a mold, the plastic substrate is covered with a membrane, and shaped against the mold as the membrane and substrate are drawn down on the mold by the vacuum. After molding, the shaped substrate is heated while maintaining the substrate under tension before being released from the mold.

I. Composition

Methods have been developed to prepare vacuum membrane thermoforms from porous substrates including poly-4-hydroxybutyrate polymer without direct exposure of the polymer to water, and preferably with less than 20% shrinkage, more preferably with less than 10% shrinkage, and even more preferably with less than 5% shrinkage, of the surface area of the substrate during thermoforming. The thermoforms are preferably formed by heating the substrate under tension, to prevent shrinkage, and molding the substrate. In a preferred embodiment, the substrate is a mesh, preferably a warp knit mesh and optionally, a polymeric film is not drawn into the pores of the mesh. The vacuum membrane thermoforms may be used as biocompatible implants, or may be converted to biocompatible implants through further processing.

A. P4HB Homopolymer

Poly-4-hydroxybutyrate and copolymers thereof can be produced using transgenic fermentation methods, see, for example, U.S. Pat. No. 6,548,569 to Williams et al., and are produced commercially, for example, by Tepha, Inc. (Lexington, Mass.). Poly-4-hydroxybutyrate is a strong, pliable thermoplastic polyester that, despite its biosynthetic route, has a relatively simple structure as shown in FIG. 1.

Although not a naturally occurring polymer, the poly-4-hydroxybutyrate polymer belongs to a larger class of materials called polyhydroxyalkanoates (PHAs) that are produced by numerous microorganisms (see, for example, Steinbüchel A., et al. Diversity of Bacterial Polyhydroxyalkanoic Acids, *FEMS Microbial. Lett.* 128:219-228 (1995)). In nature, these polyesters are produced as storage granules inside cells, and serve to regulate energy metabolism. They are also of commercial interest because of their thermoplastic properties, biodegradability and relative ease of production.

Chemical synthesis of poly-4-hydroxybutyrate has been attempted, but it has been impossible to produce the polymer with a sufficiently high molecular weight that is necessary for most applications, including melt processing (see Hori, Y., et al., *Polymer* 36:4703-4705 (1995); Houk, K. N., et al., *J. Org. Chem.*, 2008, 73 (7), 2674-2678; and Moore, T., et al., *Biomaterials* 26:3771-3782 (2005)). In fact, it has been calculated to be thermodynamically impossible to chemically synthesize a high molecular weight homopolymer under normal conditions (Moore, T., et al., *Biomaterials* 26:3771-3782 (2005)). Chemical synthesis of poly-4-hydroxybutyrate instead yields short chain oily oligomers that lack the desirable thermoplastic properties of the high molecular weight poly-4-hydroxybutyrate polymers produced by biosynthetic methods.

Poly-4-hydroxybutyrate has entirely different properties compared to poly-3hydroxybutyrate, (commonly referred to as PHB or P3HB), polylactic acid (PLA) and copolymers thereof. For example, PHB has a melting point of 180° C. versus a melting point of about 60° C. for poly-4-hydroxybutyrate. The polymers also have substantially different glass transition temperatures and mechanical properties. Poly-4-hydroxybutyrate has a glass transition temperature of −55° C. [[]]PHB is a relatively hard brittle polymer with an extension to break of just a few percent, whereas poly-4-hydroxybutyrate is a strong extensible polymer with an extension to break of about 1000%. Poly-4-hydroxybutyrate also has strikingly different uses from P3HB, as well as significantly different processing requirements.

Methods to control molecular weights of PHA polymers have been disclosed by U.S. Pat. No. 5,811,272 to Snell et al. WO 2013/049161 to Kai and Martin discloses methods to prepare poly-4-hydroxybutyrate polymers and copolymers thereof with molecular weights less than 250 kDa. The methods described herein may therefore be used to prepare poly-4-hydroxybutyrate and copolymers thereof with weight average molecular weights ($M_w$) ranging from 1 kDa to 1,200 kDa. However, more preferably the poly-4-hydroxybutyrate homopolymer and copolymers thereof that are used to make the vacuum membrane thermoforms have weight average molecular weights ranging from 50 kDa to 1,000 kDa.

Poly-4-hydroxybutyrate has been used fairly extensively in the design, development, and manufacture of medical devices, and has a good history of biocompatibility. U.S. Pat. Nos. 6,245,537, 6,623,749, 7,244,442, 7,906,135 8,231,889 and 8,771,720 to Williams et al. describe methods of making PHAs with low levels of endotoxin. U.S. Pat. No. 9,290,612 to Martin et al., U.S. Pat. No. 8,680,228 to Guo and Martin, U.S. Pat. No. 9,480,780 to Martin and Williams, US Patent Application No. 20130309275 to Carter et al., and US Patent Application No. 20070182041 to Rizk et al. disclose PHA compositions for making medical devices.

Copolymers of poly-4-hydroxybutyrate that can be used to manufacture medical devices include 4-hydroxybutyrate copolymerized with 3-hydroxybutyrate or glycolic acid (see U.S. Pat. No. 8,039,237 to Martin and Skraly, U.S. Pat. No. 6,316,262 to Huisman, et al., and U.S. Pat. No. 6,323,010 to Skraly, et al.).

U.S. Pat. Nos. 8,034,270, 8,758,657, 9,125,719 and 9,333,066 to Martin, et al. disclose methods to prepare PHA fibers and textiles, U.S. Pat. Nos. 7,943,683 and 8,753,555 to Rizk, et al. describe non-curling suture fibers made from poly-4-hydroxybutyrate, U.S. Pat. No. 8,287,909 to Martin, et al. discloses methods for melt blowing poly-4-hydroxybutyrate, U.S. Pat. Nos. 8,747,468 and 9,326,841 to Martin et al. describe coatings for PHA polymers and methods to produce fibers, US Patent Application No. 20120150285 to Cahil et al. discloses methods to dry spin poly-4-hydroxybutyrate, U.S. Pat. No. 9,149,561 to Rizk et al. describes injection molding of PHA polymers, US Patent Application No. 20140277572 to Martin et al. discloses electrospinning of poly-4-hydroxybutyrate, US Patent Application No. 20150057368 to Connelly et al. describes the preparation of closed cell foams of poly-4-hydroxybutyrate, US Patent Application No. 20150056131 to Bernasconi, et al. discloses thermoforming of poly-4-hydroxybutyrate, U.S. Pat. No. 9,302,029 to Ganatra et al. describes pultrusion of poly-4-hydroxybutyrate, US Patent Application No. 20150182670 to Rizk et al. discloses lamination of poly-4-hydroxybutyrate, U.S. Pat. No. 9,457,127 to Martin and Rizk disclose centrifugal spinning of poly-4-hydroxybutyrate, and US Patent Application No. 20160166727 to Ganatra discloses methods for orienting fibers of poly-4-hydroxybutyrate.

Applications of poly-4-hydroxybutyrate have been reviewed in Williams, S. F., et al., *Polyesters, III*, 4:91-127 (2002), Martin, D. et al. Medical Applications of Poly-4- hydroxybutyrate: A Strong Flexible Absorbable Biomaterial, *Biochem. Eng. J.* 16:97-105 (2003), Williams, S. et al. Poly-4-hydroxybutyrate (P4HB): a new generation of resorbable medical devices for tissue repair and regeneration, *Biomed. Tech.* (*Berl*) ISSN (Online) 1862-278X, ISSN (Print) 0013-5585, DOI: 10.1515/bmt-2013-0009, 2013, and Guo K. and Martin D P. Poly-4-hydroxybutyrate (P4HB) in biomedical applications and tissue engineering. In Chu C-C, ed. *Biodegradable Polymers. Volume 2: New Biomaterial Advancement and Challenges*, Hauppauge, N.Y.: Nova Science Publishers; 2015:199-231. Monofilament sutures of poly-4-hydroxybutyrate have been described by Odermatt E K, Funk L, Bargon R, Martin D P, Rizk S, Williams S F. MonoMax Suture: A new long-term absorbable monofilament suture made from poly-4-hydroxybutyrate. *Int J Polym Sci.* 2012; 12:Article ID 216137, and hernia meshes of poly-4-hydroxybutyrate have been described by Martin D P, Badhwar A, Shah D V et al. Characterization of poly-4-hydroxybutyrate mesh for hernia repair applications. *J Surg Res.* 2013; 184:766-773.

PHAs with controlled degradation and degradation in vivo of less than one year are disclosed by U.S. Pat. Nos. 6,610,764, 6,828,357, 6,867,247, 6,867,248 and 6,878,758 to Williams et al. U.S. Pat. Nos. 6,548,569, 6,838,493, 6,867,247, 7,179,883, 7,268,205, and 7,553,923 to Williams et al. describe the use of PHAs to make medical devices. U.S. Pat. Nos. 6,514,515 and 6,746,685 to Williams disclose bioabsorbable, biocompatible PHA polymers for tissue repair and engineering, U.S. Pat. Nos. 6,555,123, 6,585,994 and 7,025,980 to Williams and Martin describe the use of PHA polymers for soft tissue augmentation, US Patent Application No. 20050025809 to Hasirci and Keskin disclose the use of poly-4-hydroxybutyrate and copolymers thereof for use in drug delivery applications, US Patent Application No. 20060287659 to Terenghi et al. describe the use of poly-4-hydroxybutyrate to make nerve regeneration devices, U.S. Pat. Nos. 7,641,825 and 8,084,125 to Rizk disclose non-curling sutures comprising poly-4-hydroxybutyrate, US Patent Application No. 20060177513 to Martin et al. discloses PHA embolization devices, U.S. Pat. No. 8,016,883 to Coleman et al. describes rotator cuff repair devices made from poly-4-hydroxybutyrate, U.S. Pat. Nos. 7,618,448, 8,961,591 and 8,979,921 to Schmitz et al. disclose stents comprising poly-4-hydroxybutyrate, U.S. Pat. No. 9,216,152 to Markland et al describes injectable drug delivery systems made from PHA polymers, U.S. Pat. No. 9,162,010 to Lenarz et al. discloses poly-4-hydroxybutyrate cochlear implants that elute drugs, US Patent Application No. 20140200667 to Carter describes osteochondral implants that can be made from PHA polymers, US Patent Application No. 20150112434 to Felix discloses absorbable implants for plastic surgery, US Patent Application No. 20150018878 to Rizk describes soft suture anchors that can be manufactured from poly-4-hydroxybutyrate, US Patent Application No. 20160045636 to Rizk and Williams discloses self-retaining sutures made from poly-4-hydroxybutyrate filaments, US Patent Application No. 20150313700 to Rizk et al. describes resorbable three-dimensional implants that can be made from poly-4-hydroxybutyrate, US Patent Application No. 20160082160 to Martin et al. discloses oriented implants comprising antibiotics, and U.S. Pat. Nos. 8,858,629 and 9,277,986 to Moses et al. disclose mastopexy devices that can be manufactured from PHA polymers.

The processes described herein are used with poly-4-hydroxybutyrate homopolymer, copolymer and blends thereof. Poly-4-hydroxybutyrate homopolymer can be obtained from Tepha, Inc. of Lexington, Mass., USA. The homopolymer can have a weight average molecular weight, Mw, within the range of 50 kDa to 1,200 kDa (by GPC relative to polystyrene) and more preferably from 100 kDa to 1,000 kDa and even more preferably from 100 kDa to 600 kDa. The polymer may include the poly-4-hydroxybutyrate homopolymer blended with other absorbable polymers.

Other absorbable polymers include, but are not limited to, poly(lactides); poly(glycolide); poly(lactide-co-glycolides); poly(lactic acid); poly(glycolic acid); poly(lactic acid-co-glycolic acids); polycaprolactones; poly(orthoesters); polyanhydrides; poly(phosphazenes); polyhydroxyalkanoates (including PHB, poly-3-hydroxybutyrate-co-3-hydroxyvalerate, and poly-4-hydroxybutyrate copolymers); synthetically or biologically prepared polyesters (including polyesters with one or more of the following monomeric units: glycolic, lactic; trimethylene carbonate, p-dioxanone, or ε-caprolactone); poly(lactide-co-caprolactones); polycarbonates; tyrosine polycarbonates; polyamides (including synthetic and natural polyamides, polypeptides, and poly (amino acids)); polyesteramides; poly(dioxanones); poly (alkylene alkylates); polyethers (such as polyethylene glycol, PEG, and polyethylene oxide, PEO) or other hydrophilic or water soluble polymers such as polyvinyl pyrrolidones (PVP); polyurethanes; polyetheresters; polyacetals; polycyanoacrylates; poly(oxyethylene)/poly(oxypropylene) copolymers; polyacetals, polyketals; polyphosphates; (phosphorous-containing) polymers; polyphosphoesters; polyalkylene oxalates; polyalkylene succinates; poly(maleic acids); chitin; chitosan; modified chitosan; biocompatible polysaccharides; biocompatible copolymers (including block copolymers or random copolymers); with blocks of other biocompatible or biodegradable polymers, for example, poly(lactide), poly(lactide-co-glycolide, or polycaprolcatone or combinations thereof.

In a preferred method, the poly-4-hydroxybutyrate homopolymer, copolymer, and blends thereof may be converted into pellets prior to making substrates suitable for thermoforming. Pellets may be compounded by metering in the desired ratio of polymers into a single or twin-screw extruder, wherein they are mixed prior to being extruded into pellets. The poly-4-hydroxybutyrate polymer, copolymer and blends thereof may also be used in powder or granular form.

In a preferred embodiment, the pellets or granules are used to prepare fibers, preferably highly oriented fibers, that are made into porous substrates for thermoforming. In an even more preferred embodiment, the poly-4-hydroxybutyrate polymer, copolymer or blend thereof is converted into oriented monofilament fibers that are knit to form a monofilament mesh suitable for vacuum membrane thermoforming.

B. Incorporation of Additives into Poly-4-Hydroxybutyrate Homopolymer, Copolymer and Blends Thereof Certain additives may be incorporated into the poly-4-hydroxybutyrate homopolymer, copolymer and blends thereof prior to converting these compositions into substrates suitable for vacuum membrane thermoforming. Preferably, these additives are incorporated during the compounding process to produce powder or pellets for further processing. In another embodiment, these additives may be incorporated using a solution-based process, for example, fiber may be solution spun from solutions that include additives and poly-4-hydroxybutyrate or copolymers thereof. In a preferred embodiment, the additives are biocompatible, and even more preferably the additives are both biocompatible and resorbable.

In one embodiment, the additives may be nucleating agents and/or plasticizers. These additives may be added in sufficient quantity to produce the desired result. In general, these additives may be added in amounts of up to 20% by weight. Nucleating agents may be incorporated to increase the rate of crystallization of the poly-4-hydroxybutyrate homopolymer copolymer or blend thereof. Such agents may be used to improve the mechanical properties of the substrates to be thermoformed and resulting thermoforms, and to reduce cycle times. Preferred nucleating agents include, but are not limited to, salts of organic acids such as calcium citrate, polymers or oligomers of PHA polymers and copolymers, high melting polymers such as PGA, talc, micronized mica, calcium carbonate, ammonium chloride, and aromatic amino acids such as tyrosine and phenylalanine. Plasticizers that may be incorporated include, but are not limited to, di-n-butyl maleate, methyl laureate, dibutyl fumarate, di(2-ethylhexyl) (dioctyl) maleate, paraffin, dodecanol, olive oil, soybean oil, polytetramethylene glycols, methyl oleate, n-propyl oleate, tetrahydofurfuryl oleate, epoxidized linseed oil, 2-ethyl hexyl epoxytallate, glycerol triacetate, methyl linoleate, dibutyl fumarate, methyl acetyl ricinoleate, acetyl tri(n-butyl) citrate, acetyl triethyl citrate, tri(n-butyl) citrate, triethyl citrate, bis(2-hydroxyethyl) dimerate, butyl ricinoleate, glyceryl tri-(acetyl ricinoleate), methyl ricinoleate, n-butyl acetyl rincinoleate, propylene glycol ricinoleate, diethyl succinate, diisobutyl adipate, dimethyl azelate, di(n-hexyl) azelate, tri-butyl phosphate, and mixtures thereof. Particularly preferred plasticizers are citrate esters.

In another preferred embodiment, the additives are contrast agents, radiopaque markers or radioactive substances. These additives may also be incorporated into the poly-4-hydroxybutyrate homopolymer, copolymer, and blend thereof either before preparing the substrates for thermoforming or after thermoforming.

In yet another preferred embodiment, the additives are ceramics, more preferably bioceramics, and even more preferably resorbable bioceramics. Examples of resorbable bioceramics that can be incorporated into blends with poly-4-hydroxybutyrate and copolymers thereof include tricalcium phosphate ($\alpha$ and $\beta$ forms of tricalcium phosphate (TCP)—with a nominal composition of $Ca_3(PO_4)_2$), biphasic calcium phosphate (BCP), hydroxylapatite, calcium sulfate, calcium carbonate, and other calcium phosphate salt-based bioceramics. Bio-active glasses may also be used. Bioactive glasses include bioactive glasses composed of $SiO_2$, $Na_2O$, $CaO$ and $P_2O_5$ in specific proportions. In a preferred embodiment, the poly-4-hydroxybutyrate blends comprise resorbable bioceramics with a size distribution ranging from nanoparticles to microparticles. In a preferred embodiment, the ceramics have particle sizes of less than 100 microns. In a particularly preferred embodiment, the poly-4-hydroxybutyrate blends include $\beta$-TCP, $\alpha$-TCP or a combination thereof.

C. Incorporation of Bioactive Agents into Poly-4-Hydroxybutyrate Polymer and Blends Thereof If desired, the poly-4-hydroxybutyrate homopolymer, copolymer, and blends thereof that are used to make the thermoforms may incorporate bioactive agents. These agents may be added during the formulation process, during pelletization, or may be added later to the substrates to be thermoformed or the thermoforms.

In one embodiment, the bioactive agents, the poly-4-hydroxybutyrate homopolymer, copolymer or blend thereof, may be dissolved in a solvent or solvent system in order to disperse the bioactive agent in the polymer or copolymer, and the solvent may then be removed by evaporation. Preferred solvents include methylene chloride, chloroform, tetrahydrofuran, acetone, dimethylformamide, and 1,4-dioxane.

Examples of bioactive agents that can be incorporated into the poly-4-hydroxybutyrate polymer and copolymer, include, but are not limited to, biologically, physiologically or pharmacologically active substances that act locally or systemically in the human or animal body. Examples can include, but are not limited to, small-molecule drugs, anti-inflammatory agents, immunomodulatory agents, molecules that promote cell migration, molecules that promote or retard cell division, molecules that promote or retard cell proliferation and differentiation, molecules that stimulate phenotypic modification of cells, molecules that promote or retard angiogenesis, molecules that promote or retard vascularization, molecules that promote or retard extracellular matrix disposition, signaling ligands, platelet rich plasma, peptides, proteins, glycoproteins, anesthetics, hormones, antibodies, growth factors, fibronectin, laminin, vitronectin, integrins, antibiotics, steroids, hydroxyapatite, silver particles, vitamins, non-steroidal anti-inflammatory drugs, chitosan and derivatives thereof, alginate and derivatives thereof, collagen, sugars, polysaccharides, nucleotides, oligonucleotides, lipids, lipoproteins, hyaluronic acid and derivatives thereof, allograft material, xenograft material, ceramics, nucleic acid molecules, antisense molecules, aptamers, siRNA, nucleic acids, and combinations thereof.

II. Methods of Preparing Substrates Including Poly-4-Hydroxybutyrate and Copolymers Thereof for Vacuum Membrane Thermoforming The poly-4-hydroxybutyrate polymer, copolymer or blend thereof may be converted into a suitable substrate for vacuum membrane thermoforming by any suitable method, including extrusion, solvent spinning, solvent casting, injection molding and compression molding. In a preferred embodiment, the substrate is porous. In a particularly preferred embodiment the substrate is formed from oriented fibers of poly-4-hydroxybutyrate polymer, copolymer or blend thereof. In an even more preferred embodiment the substrate for vacuum membrane thermoforming is an oriented mesh comprising monofilament fibers of poly-4-hydroxybutyrate polymer, copolymer or blend thereof and does not include a film.

In a preferred method, the porous substrate including poly-4-hydroxybutyrate, copolymer, or blend thereof is extruded either directly from a powder or granular form, or even more preferably from pellets including poly-4-hydroxybutyrate, copolymer or blend thereof. A particularly preferred substrate is a mesh.

In a particularly preferred method, powder, granules or pellets including poly-4-hydroxybutyrate, copolymer or blend thereof are dried prior to melt extrusion in order to limit the loss of intrinsic viscosity of the polymer or copolymer during processing. The specific extent of drying necessary depends on the loss of intrinsic viscosity that can be tolerated for a particular application. In an embodiment, the polymer, copolymer, or blend to be melt-extruded is dried such that the moisture content of the polymer, copolymer, or blend is no greater than 0.5% by weight as measured gravimetrically, and more preferably no greater than 0.05% by weight. The polymer, copolymer, or blend may be dried in vacuo. In a particularly preferred method, the polymer or blend is dried in a vacuum chamber under a vacuum of at least 10 mbar, more preferably of at least 0.8 mbar, to a moisture content of less than 0.03% by weight. Elevated temperatures below the melting point of the polymer pellets may also be used in the drying process. Alternatively, the polymer may be dried by extraction into a solvent and re-precipitation, or with the use of desiccants. The moisture content of samples including poly-4-hydroxybutyrate, copolymer or blend thereof may be determined using a VaporPro Moisture Analyzer from Arizona Instruments, or similar instrument, as follows. Samples should be transferred to test vials in a low humidity environment (<5% RH) to minimize pickup of ambient moisture. Samples (1 g) can then be heated to 120° C. under a purge of dry nitrogen. The moisture content of the purge gas is determined by the Vapor Pro and reported as a % of the sample weight.

Melt-extrusion or solvent spinning may be used to prepare fibers of poly-4-hydroxybutyrate, copolymer or blend thereof, suitable for forming porous substrates for vacuum membrane thermoforming. Poly-4-hydroxybutyrate monofilament fibers are made by melt extrusion, for example, as described by WO 2011/119742 to Martin et al. and U.S. Pat. No. 8,034,270 to Martin et al. The diameters of the poly-4-hydroxybutyrate monofilament fibers may range from 10 µm to 1 mm, but more preferably have a diameter ranging from 50 µm to 600 µm, and even more preferably from 50 µm to 250 µm. In another embodiment, the monofilament fibers are USP sizes 5, 4, 3, 2, 1, 0, 2-0, 3-0, 4-0, 5-0, 6-0, 7-0, 8-0, 9-0, 10-0, 11-0 and 12-0 as defined by the United States Pharmacopeia (USP) for absorbable monofilament sutures. In a preferred embodiment, the poly-4-hydroxybutyrate fibers are oriented. The exact mechanical properties of the fibers will depend upon the degree of orientation. In a particularly preferred embodiment, the oriented poly-4-hydroxybutyrate monofilament fiber will have one or more of the following properties: a tensile strength of at least 100 MPa, more preferably at least 300 MPa, and even more preferably at least 500 MPa, 600 MPa, 700 MPa, 800 MPa, 900 MPa, 1,000 MPa, 1,100 MPa, 1,200 MPa, 1,300 MPa, 1,400 MPa but less than 1,500 MPa; a break strength between 0.01 Kg and 100 Kg, more preferably between 0.1 Kg and 40 Kg; an elongation to break of less than 500%, more preferably less than 300%, and even more preferably less than 100%, but greater than 3%; a tensile modulus of at least 100 MPa, more preferably at least 300 MPa, and even more preferably 500 MPa, but less than 2 GPa.

In another embodiment, the substrates for thermoforming may comprise multifilament fibers of poly-4-hydroxybutyrate, or copolymer thereof. Poly-4-hydroxybutyrate multifilament fibers may be prepared by melt extrusion or solution spinning. In a preferred embodiment, the poly-4-hydroxybutyrate multifilament fibers are made by melt extrusion, and may be prepared as described by WO 2011/119742 to Martin et al. and U.S. Pat. No. 8,034,270 to Martin et al. In an embodiment, the poly-4-hydroxybutyrate multifilament fibers are prepared with a denier per filament (dpf) of less than 10, preferably less than 6, and even more preferably less than 3, but greater than 1. In a particularly preferred embodiment, the multifilament fibers have a denier per filament ranging from 1.7 to 9.0. In another embodiment, the multifilament fibers are prepared with a tenacity of greater than 2 grams/denier, and more preferably greater than 4 grams/denier, and even more preferably greater than 9 or 9.5 grams per denier. In some embodiments, the poly-4-hydroxybutyrate multifilaments have a tenacity greater than 2 but less than 12. In another embodiment, the poly-4-hydroxybutyrate multifilaments have an average elongation to break of 10% to 70%, more preferably 10% to 40%.

Oriented poly-4-hydroxybutyrate monofilament meshes for vacuum membrane thermoforming may be made as disclosed by WO 2011/119742 to Martin and U.S. Pat. No. 8,034,270 to Martin et al.

In an embodiment, the poly-4-hydroxybutyrate meshes have one or more of the following properties: an average thickness greater than 0.01 mm; an average thickness less than 25 mm; an average thickness between 0.01 mm and 25 mm; average pore sizes greater than 0.01 mm in diameter; average pore sizes less than 10 mm in diameter; average pore sizes between 0.01 mm and less than 10 mm in diameter, including average pore sizes greater than 0.1 mm in diameter and greater than 1 mm in diameter; a density of pores between 1 and 50 per square cm, including greater than 5, 10, 15, 20, 25, 30, 35, 40, and 45 per square cm; burst strength greater than 1 Kgf; burst strength less than 100 Kgf; burst strength between 1 Kgf and 100 Kgf, including greater than 5, 10, 15, 20, 25, 30, 35, 40, 45, 50, 55, 60, 65, 70, 75, 80, 85, 90, 95 Kgf; a Taber stiffness that is less than 100 Taber stiffness units, and more preferably less than 10 Taber stiffness units; and a suture pullout strength of at least 10 N, and more preferably at least 20 N, but less than 1,000 N. The mesh preferably has an areal density of 5 to 800 g/m$^2$.

In a preferred embodiment, the poly-4-hydroxybutyrate mesh is made from poly-4-hydroxybutyrate monofilament fibers. In a more preferred embodiment, the poly-4-hydroxybutyrate monofilament mesh has a knitted or woven structure. A particularly preferred poly-4-hydroxybutyrate monofilament mesh has substantially one or more of the following properties: an average pore diameter of approximately 500 µm±100 µm, thickness of 0.5 mm±0.1 mm, areal density of 182 g/m$^2$±40 g/m$^2$, suture pullout strength of 5.6 Kgf±1.2 Kgf, and a burst strength of 24.5 Kg±5 Kg.

In another preferred embodiment, the meshes of poly-4-hydroxybutyrate or copolymer thereof are produced by either warp or weft knitting processes, however, a warp knit is preferred in order to minimize the stretching of the mesh structure.

In another embodiment, the meshes of poly-4-hydroxybutyrate or copolymer thereof may comprise different sized fibers or other non-poly-4-hydroxybutyrate fibers, including PHA multifilament, and fibers made from other absorbable or non-absorbable biocompatible polymers and hybrid meshes.

A suitable knitted poly-4-hydroxybutyrate mesh may be prepared, for example, as follows: monofilament poly-4-hydroxybutyrate fibers are mounted on a creel, aligned side by side and pulled under uniform tension to the upper surface of a "kiss" roller. The "kiss" roller is spun while semi-immersed in a bath filled with a 10% solution of Tween® 20 lubricant. The Tween® 20 lubricant is deposited on the surface of the sheet of fiber. Following the application of Tween® 20, the sheet of fiber is passed into a comb guide and then wound on a warp beam. A warp is a large cylinder onto which individual fibers are wound in parallel to provide a sheet of fibers. Next, warp beams are converted into a finished mesh fabric by means of interlocking knit loops. Eight warp beams are mounted in parallel onto tricot machine let-offs and fed into the knitting elements at a constant rate determined by the "runner length". Each individual monofilament fiber from each beam is fed through a series of dynamic tension elements down into the knitting "guides". Each fiber is passed through a single guide, which is fixed to a guide bar. The guide bar directs the fibers around the needles forming the mesh fabric structure. The mesh fabric is then pulled off the needles by the take down rollers at a constant rate of speed determined by the fabric "quality". The mesh fabric is then taken up and wound onto a roll ready for scouring. The poly-4-hydroxybutyate monofilament mesh may be scoured ultrasonically with water, and heat set in hot water if desired. The mesh can be washed with a 70% aqueous ethanol solution.

III. Vacuum Membrane Thermoforming of Substrates Containing Poly-4-Hydroxybutyrate Homopolymer, Copolymer and Blends Thereof US Patent Application No. 20150056131 to Bernasconi et al. discloses thermoforming non-porous substrates (a mesh is converted into a non-porous substrate by covering the mesh surface with a film) of poly-4-hydroxybutyrate. The method involves heating a film, sheet or laminate of a film and mesh including poly-4-ydroxybutyrate to at least its softening temperature, more preferably its melting temperature, and thermoforming the substrate using a mold. In a typical procedure, a film including poly-4-hydroxybutyrate is heated to at least 51.9° C., placed over the desired mold, and pulled or pushed into place by means of a vacuum or applied pressure.

It has been discovered that porous substrates including poly-4-hydroxybutyrate can be thermoformed using vacuum membrane thermoforming. More preferably, oriented poly-4-hydroxybutyrate meshes can be shaped by this method without shrinkage of the mesh, without loss of tensile properties of the mesh, and without the use of water. The disclosed method differs from the process described in US Patent Application No. 20150056131 to Bernasconi, et al., as shown in the Table below, in the following respects: (i) porous substrates are thermoformed in the disclosed method; by contrast non-porous substrates, namely films, sheets and laminates of film with mesh are thermoformed in Bernasconi et al.; the film is drawn into the pores of the mesh during thermoforming, resulting in a non-porous structure (ii) heat is not applied to the porous substrate before the vacuum is applied in the disclosed method whereas Bernasconi, et al. heat the non-porous substrate prior to applying a vacuum, (iii) a membrane is used as a seal in the disclosed method to make it possible to apply pressure to the porous substrate and vacuum thermoform the porous substrate, whereas Bernasconi does not use a membrane to thermoform non-porous substrates, and (iv) not only does the membrane allow a vacuum to be applied to shape the porous substrate, it also allows tension to be applied to the porous substrate that prevents the porous substrate from shrinking when heat is applied to mold the porous substrate.

| Bernasconi, et al. US Patent Application No. 20150056131 | Disclosed method |
|---|---|
| Non-porous substrate (e.g. film or sheet) is thermoformed | Porous substrate (e.g. mesh) is thermoformed |
| Film or sheet is heated prior to shaping and applying vacuum | Mesh is heated after shaping by applying vacuum |
| No membrane is used to cover the sheet or film | Membrane is used to render the porous substrate impermeable |
| Membrane is not used to apply tension to film or sheet to prevent shrinkage | Membrane is used to apply tension to the mesh to prevent shrinkage |

Comparative Example 2, based on the method of Bernasconi et al., demonstrates the importance of heating an oriented poly-4-hydroxybutyrate mesh only after tension has been applied to the mesh by application of the vacuum. Comparative Example 2 demonstrates that shrinkage of the mesh will result if the mesh is heated before tension is applied to the mesh. In contrast, Example 1 shows that no shrinkage occurs when tension is applied to the mesh (i.e., the mesh is constrained between the membrane and mold by application of the vacuum) before the mesh is heated.

Additional advantages of the disclosed method are the following: (i) the method is fast and inexpensive, (ii) the non-porous substrate does not come into contact with water and therefore reduces the likelihood that the substrate will become contaminated, for example, with endotoxin, or degraded in the case of a resorbable non-porous substrate, (iii) complex shapes with undercuts can be easily made using inexpensive molds, and (iv) the method can easily be performed in a clean room.

In a typical procedure for vacuum membrane thermoforming of a porous substrate, such as an oriented monofilament mesh, the mesh is draped over a mold, and covered with a membrane so that the mesh is sandwiched between the mold and the membrane. The membrane must be flexible enough to contour to the shape of the mold and impervious so it can be drawn down on the mold, but not into the pores of the mesh, when a vacuum is applied. Films such as P4HB films are not considered "a membrane" for this step, because the heated film will be drawn into the pores of the mesh during thermoforming. Accordingly, the vacuum membrane thermoforming disclosed therein does not include placing a P4HB film over the mesh prior to themoforming. A suitable membrane is made of silicone. Once the membrane is positioned over the mold and mesh, it is drawn down onto the mesh and mold by applying a vacuum. The vacuum should be strong enough to apply tension to the mesh so that it cannot move, particularly when heat is applied in the next step of the process. In the absence of tension, the mesh will shrink when heat is applied, and porosity will be compromised. An example of a suitable vacuum for vacuum membrane thermoforming of an oriented poly-4-hydroxybutyrate monofilament mesh is 0.1-100 mmHg, more preferably 1-50 mmHg Once the mesh has been shaped on the mold by the pressure of the membrane, heat may be applied to the shaped mesh in order to mold it permanently into the desired shape. The mesh may be heated by heating the mold, applying heat through the membrane, or both. In the case of vacuum membrane thermoforming of an oriented poly-4-hydroxybutyrate monofilament mesh, the mesh is heated to at least 52° C., more preferably above 60° C., but less than 110° C. The mesh should be heated long enough and at a sufficient temperature to ensure that it maintains its molded shape permanently when cooled, but not at a temperature that could cause de-orientation of the mesh fibers and loss of strength. The exact heating time will depend upon: the temperature of the heaters, initial temperature of the mold/mesh/membrane assembly, effective heat transfer coefficient of the assembly, mesh thickness, and thermal properties of the mesh. A suitable heating time is up to 10 minutes, but more preferably less than 6 minutes. During heating, it is important to maintain tension on the mesh by continuous application of the vacuum. After heating, the mesh should be allowed time to cool before the vacuum is released and the mesh is removed from the mold. This will ensure that the mesh can be removed from the mold without de-orientation of the mesh fibers resulting in loss of mechanical properties and the integrity of the mesh being compromised. The cooling time should preferably be as short as possible. In a preferred embodiment, the mold is rapidly cooled. In a particularly preferred embodiment, the mold is cooled to −20° C. to 20° C. If desired, the resulting thermoform may be put through additional heating cycles and cooling cycles to stabilize the thermoform. Typical heating temperatures are between ambient and 110° C., and typical cooling temperatures are between −20 to 20° C.

IV. Medical Implants of Vacuum Membrane Thermoforms Including P4HB

Vacuum membrane thermoforming of porous substrates including oriented poly-4-hydroxybutyrate allows implants of highly oriented poly-4-hydroxybutyrate to be prepared which is particularly advantageous when orientation is necessary in more than one direction of the implant.

Implants made from vacuum membrane thermoforms including P4HB polymer, copolymer and blends thereof, may be used for soft and hard tissue repair, regeneration, and replacement. These implants may be used in the following medical devices, including, but not limited to, organ salvage device, dural substitute, hernia repair device, hernia mesh, hernia plug, tissue engineering scaffold, guided tissue repair/regeneration device, knitted and woven surgical meshes, slings, device for pelvic floor reconstruction, urethral suspension device, device for treatment of urinary incontinence, ligament repair device, tendon repair device, myocardial regeneration device, cell seeded device, controlled release device, drug delivery device, plastic surgery device, breast lift device, mastopexy device, breast reconstruction device, breast augmentation device (including devices for use with breast implants), breast reduction device (including devices for removal, reshaping and reorienting breast tissue), devices for breast reconstruction following mastectomy with or without breast implants, buttock lift device, thigh lift device, arm lift device, facial reconstructive device, forehead lift device, brow lift device, eyelid lift device, face lift device, rhytidectomy device, and neck lift device.

The implants may be made directly in the vacuum membrane molding process, or the thermoform may be subsequently converted into the desired device. In a particularly preferred embodiment, highly oriented thermoforms of poly-4-hydroxybutyrate are manufactured, and used directly as implants. Particularly preferred implants are three-dimensional meshes comprising oriented poly-4-hydroxybutyrate fibers for hernia repair, mastopexy, breast reconstruction, and pelvic floor reconstruction.

The present invention will be further understood by reference to the following non-limiting examples.

Example 1: Vacuum Membrane Thermoforming of a Poly-4-hydroxybutyrate Oriented Monofilament Mesh A poly-4-hydroxybutyrate oriented monofilament warp knitted mesh, fiber diameter approx. 160 µm, pore size 2.58 mm$^2$, thickness 0.508 mm, areal density 182 g/m$^2$, ball burst strength 24.54 Kgf with 3/8 in ball, suture pullout strength 5.6 kgf, was vacuum membrane thermoformed using a vacuum membrane table (GEN III PLUG-N-PLAY Vacuum Press, item number VCMPRS1, RC Holster supply). The vacuum membrane equipment was connected to a four stage Teflon membrane vacuum pump. The poly-4-hydroxybutyrate mesh was cut into a rectangle of approximately 20.5×12 cm. This cut piece of mesh was placed on the vacuum forming table over a metal mold. The lid was closed to cover the mesh with the vacuum membrane and a vacuum (95 kPa, 28 mm Hg) was applied to the membrane to provide tension on the mesh. The mesh was heated by placing a bag containing heated water (65° C.) for 3 minutes on the membrane covering the mesh. (This method allowed a heat transfer fluid to be placed in indirect contact with the mesh, and avoided direct contact of the heat transfer fluid with the mesh.) A digital temperature probe was placed between the bag and the mesh to record the temperature of the mesh. During heating, the thermocouple recorded a maximum temperature of 61.6° C. Thereafter, the heating bag was removed and replaced with a cold compress containing ice water. The sample was cooled until the digital probe showed the mesh had cooled to less than 10° C. for at least one minute. The cold compress was removed, the pressure was released and the membrane was lifted off of the molded mesh. The molded mesh did not show signs of uncontrolled shrinkage and retained the porous structure of the mesh.

Comparative Example 2: Thermoforming of a Poly-4-hydroxybutyrate Oriented Monofilament Mesh by Application of Heat Without Applying Tension to the Mesh A P4HB mesh was cut into a rectangle of approximate 20.5×10 cm. This cut piece of mesh was placed on the vacuum forming table over a metal mold as described in Example 1. The mesh was covered with a bag containing heated water (which applies pressure to the mesh) as described in Example 1. A digital temperature probe was placed between the bag and the mesh to record the temperature of the mesh. During heating, the thermocouple recorded a maximum temperature of 56.6° C. Thereafter, the heating bag was removed and replaced with a cold compress containing ice water as described in Example 1. The sample was cooled until the thermocouple showed the mesh had cooled to less than 10° C. for at least one minute, then the cold compress was removed and inspected. The thermoformed mesh was observed to have shrunk and also lost its uniform porous structure.

We claim:

1. A method of making an implant comprising a porous thermoform of poly-4-hydroxybutyrate homopolymer, copolymer, or blend thereof by vacuum membrane thermoforming comprising:
   (a) placing a porous substrate of poly-4-hydroxybutyrate homopolymer, copolymer or blend thereof on a mold,
   (b) covering the substrate with an impermeable flexible membrane,
   (c) applying tension to the substrate and impermeable flexible membrane by drawing down the substrate onto the mold by applying a vacuum,
   (d) heating the substrate under the applied tension to form a porous thermoform,
   (e) allowing the thermoform to cool, wherein the thermoform and impermeable membrane are released from the vacuum, the impermeable flexible membrane is removed from the mold and the thermoform is removed from the mold.

2. The method of claim 1, wherein the substrate is heated to at least 52° C. but less than 110° C.

3. The method of claim 1, wherein the substrate is an oriented monofilament poly-4-hydroxybutyrate mesh.

4. The method of claim 1, wherein the substrate does not come into contact with liquid and remains dry during thermoforming.

5. The method of claim 1 wherein the poly-4-hydroxybutyrate homopolymer or copolymer is produced by a microorganism or enzymatic process.

6. The method of claim 1 wherein the substrate is heated at a temperature above 60° C., but less than 110° C.

7. The method of claim 1 wherein the substrate is a mesh, and wherein a polymeric film is not drawn into the pores of the mesh.

8. The method of claim 7 wherein the mesh is made of oriented monofilament fibers.

9. The method of claim 8 wherein the mesh has one or more properties selected from the group consisting of: an average pore diameter of approximately 500 µm ±100 µm, a thickness of 0.5 mm ±0.1 mm, an areal density of 182 g/m$^2$±40 g/m$^2$, a suture pullout strength of 5.6 Kgf ±1.2 Kgf, and a burst strength of 24.5 Kg ±5 Kg.

10. The method of claim 1 wherein the substrate comprises one or more agents selected from the group consisting of a nucleant, a plasticizer, a ceramic, a bioactive agent, an antimicrobial agent, a contrast agent, a radiopaque marker and a radioactive substance.

11. The method of claim 1 wherein the substrate is a woven mesh, or a knitted mesh.

12. The method of claim 1 wherein the implant is selected from the group consisting of a patch, wound healing device, bandage, wound dressing, burn dressing, ulcer dressing, skin substitute, hemostat, tracheal reconstruction device, organ salvage device, pledgets, dural substitute, dural patch, nerve guide, nerve regeneration or repair device, hernia repair device, hernia mesh, hernia plug, device for temporary wound or tissue support, tissue engineering scaffold, guided tissue repair or regeneration device, laminated knitted meshes, woven meshes, non-woven meshes, fixation device for meshes, anti-adhesion membrane, adhesion barrier, tissue separation membrane, retention membrane, catheter, sling, device for pelvic floor reconstruction, urethral suspension device, device for treatment of urinary incontinence, device for treatment of vesicoureteral reflux, bladder repair device, sphincter muscle repair device, bulking or filling device, bone marrow scaffold, clip, clamp, screw, pin, locking pin, nail, tube, medullary cavity nail, bone plate, interference screw, tack, arrow, fastener, rivet, staple, fixation device for an implant, bone graft substitute, bone void filler, suture anchor, bone anchor, ligament repair device, ligament augmentation device, ligament graft, anterior cruciate ligament repair device, tendon repair device, tendon graft, tendon augmentation device, rotator cuff repair device, meniscus repair device, meniscus regeneration device, articular cartilage repair device, osteochondral repair device, spinal fusion device, vertebral disc, cage, device for treatment of osteoarthritis, viscosupplement, stent, coronary stent, cardiovascular stent, peripheral stent, ureteric stent, urethral stent, urology stent, gastroenterology stent, nasal stent, ocular stent, neurology stents, stent coatings, stent graft, cardiovascular patch, catheter balloon, vascular closure device, intracardiac septal defect repair device, atrial septal defect repair device, patent foramen ovale closure device, left atrial appendage closure device, pericardial patch, vein valve, heart valve, vascular graft, myocardial regeneration device, periodontal mesh, guided tissue regeneration membrane for periodontal tissue, ocular cell implant, imaging device, cochlear implant, embolization device, anastomosis device, cell seeded device, cell encapsulation device, controlled release device, drug delivery device, plastic surgery device, breast lift device, mastopexy device, breast reconstruction device, breast augmentation device breast reduction device, device for removal, reshaping and reorienting breast tissue, device for breast reconstruction following mastectomy, facial reconstructive device, forehead lift device, brow lift device, eyelid lift device, face lift device, buttock lift device, thigh lift device, arm lift device, rhytidectomy device, thread lift device, rhinoplasty device, device for malar augmentation, otoplasty device, neck lift device, mentoplasty device, cosmetic repair device, and device for facial scar revision.

\* \* \* \* \*